(12) United States Patent
Pendleton et al.

(10) Patent No.: US 8,916,731 B2
(45) Date of Patent: Dec. 23, 2014

(54) DIALKYL AND DIARYL ETHER PRODUCTION FROM METAL ALCOHOLATE

(75) Inventors: Justin Pendleton, Salt Lake City, UT (US); Sai Bhavaraju, West Jordan, UT (US)

(73) Assignee: Ceramatec, Inc., Salt Lake City, UT (US)

( * ) Notice: Subject to any disclaimer, the term of this patent is extended or adjusted under 35 U.S.C. 154(b) by 634 days.

(21) Appl. No.: 12/834,679

(22) Filed: Jul. 12, 2010

(65) Prior Publication Data

US 2011/0015449 A1   Jan. 20, 2011

Related U.S. Application Data

(60) Provisional application No. 61/225,465, filed on Jul. 14, 2009.

(51) Int. Cl.
| | |
|---|---|
| *C07C 41/09* | (2006.01) |
| *C07C 29/70* | (2006.01) |
| *C07C 41/01* | (2006.01) |
| *C07C 37/66* | (2006.01) |

(52) U.S. Cl.
CPC .............. *C07C 41/01* (2013.01); *C07C 29/70* (2013.01); *C07C 37/66* (2013.01)
USPC ............................. 568/698; 568/632; 568/635

(58) Field of Classification Search
None
See application file for complete search history.

(56) References Cited

U.S. PATENT DOCUMENTS

| | | | | |
|---|---|---|---|---|
| 2,069,403 | A | * | 2/1937 | Cunningham ................ 205/450 |
| 2,784,201 | A | * | 3/1957 | Chitwood ...................... 549/230 |
| 2,860,170 | A | * | 11/1958 | Criscione et al. ............. 568/671 |
| 3,642,866 | A | * | 2/1972 | Witt et al. ........................ 560/64 |
| 3,809,648 | A | * | 5/1974 | Hotten .......................... 508/375 |
| 4,540,679 | A | * | 9/1985 | Arzoumanidis et al. ...... 502/111 |
| 5,189,203 | A | | 2/1993 | Hansen et al. |
| 2007/0055042 | A1 | * | 3/2007 | Miyake et al. ................ 528/196 |

OTHER PUBLICATIONS

Jeong, Sei J., "International Search Report", PCT/US2010/041746, (Feb. 21, 2011),1-3.
Jeong, Sei J., "Written Opinion of the International Seaching Authority", PCT/US2010/041746, (Feb. 21, 2011),1-3.

* cited by examiner

*Primary Examiner* — Rosalynd Keys
(74) *Attorney, Agent, or Firm* — David Fonda

(57) ABSTRACT

A dialkyl or diaryl ether is produced by reacting carbon dioxide with a metal alcoholate having the formula, $M(RO)_x$, where "M" is a Group 1, Group 2, or Group 3 metal; "x" is the valence of the metal M; "R" is a $C_1$ to $C_6$ lower alkyl or aryl, wherein the reaction produces a dialkyl or diaryl ether having a formula, R—O—R, and a metal carbonate having a formula $M_2CO_3$ where M is a Group 1 metal, $MCO_3$ where M is a Group 2 metal, and $M_2(CO_3)_3$ where M is a Group 3 metal. The metal carbonate may be removed by conventional means, such as filtration. The dialkyl or diaryl ether may be recovered and used as a fuel, fuel additive, propellant, or building block for other fuels or petrochemicals. In some cases the metal alcoholate is in an alcohol solution and the alcohol and metal carbonate are recycled to regenerate the metal alcoholate. A specific example of dimethyl ether production is disclosed.

17 Claims, 1 Drawing Sheet

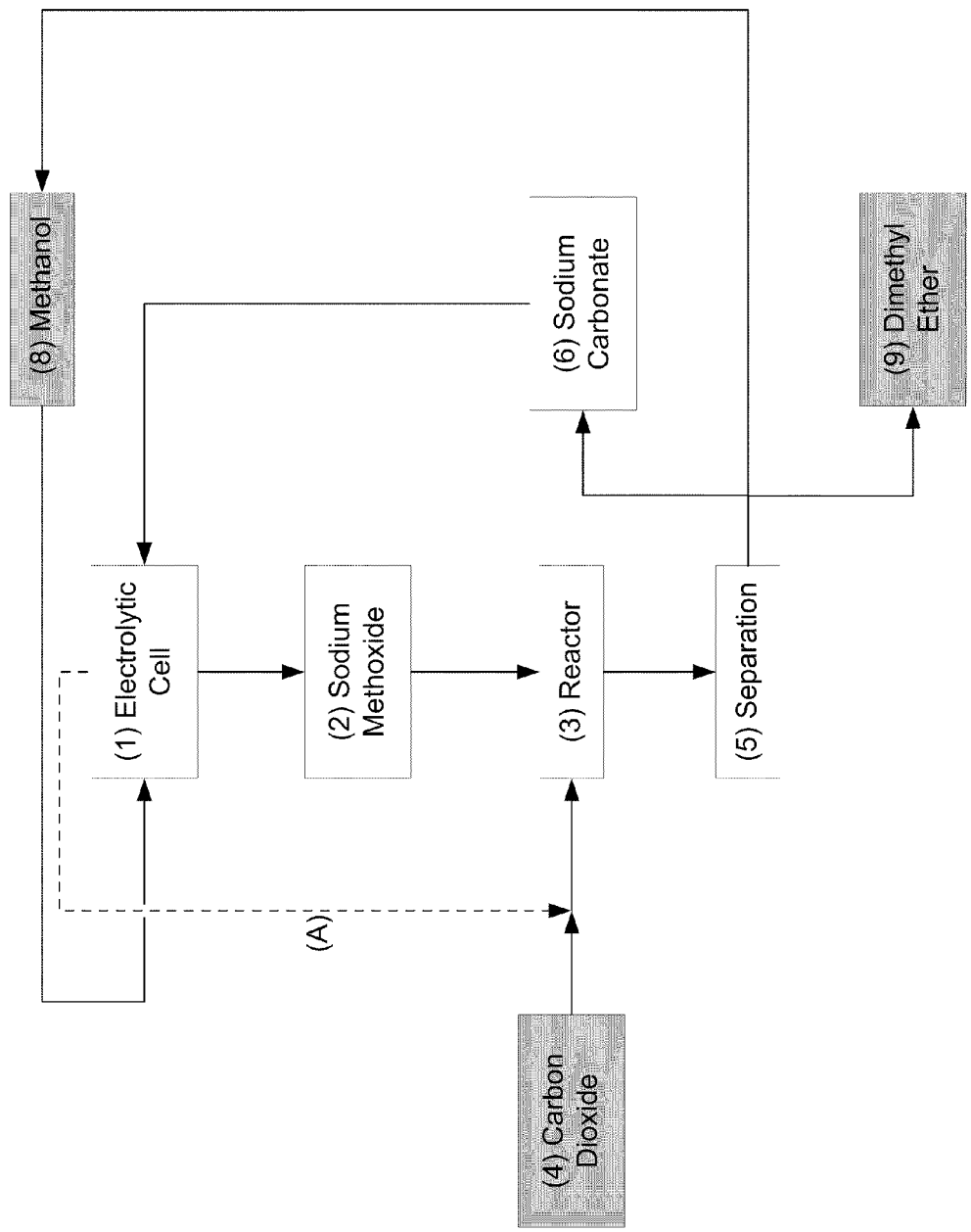

DIALKYL AND DIARYL ETHER PRODUCTION FROM METAL ALCOHOLATE

CROSS-REFERENCE TO RELATED APPLICATION

This application claims the benefit of Provisional Application No. 61/225,465, filed Jul. 14, 2009, entitled "Dimethyl Ether Production from Sodium Methoxide," the entire disclosure of which is hereby incorporated by reference.

BACKGROUND OF THE INVENTION

The invention relates to a process to produce dialkyl and diaryl ethers. The disclosed process includes the reaction of carbon dioxide with a metal alcoholate, also known as a metal alkoxide, to form the dialkyl and diaryl ethers. A specific example of dimethyl ether (DME) production is disclosed.

Dimethyl ether (DME) is a clean burning fuel that can be used in diesel engines or as an additive to diesel fuel. The cetane number is slightly higher than diesel and can be stored and transported like liquid petroleum gas (LPG). It liquefies at $-25°$ C. or about 6 atmospheres. Burning DME in diesel engines results in a lower NOx with no SOx.

Dimethyl ether can be substituted for liquefied petroleum gas (LPG), as a blended fuel, or reformed into hydrogen for fuel cells. DME has been increasingly used as a propellant in aerosol formulations to replace chlorofuorocarbons. DME is becoming a promising building block in the fuel and petrochemical industry.

One conventional production method of DME derives from synthesis gas (hydrogen and carbon monoxide) reacted over a mixed catalyst reactor at high temperature and pressure. Conversion rates per pass over the catalyst are as low as 18 to 50 percent. The reaction formulas and reaction heat concerning DME synthesis are as follows:

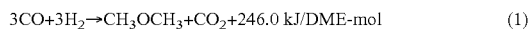
$$3CO+3H_2 \rightarrow CH_3OCH_3+CO_2+246.0 \text{ kJ/DME-mol} \quad (1)$$

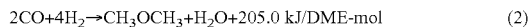
$$2CO+4H_2 \rightarrow CH_3OCH_3+H_2O+205.0 \text{ kJ/DME-mol} \quad (2)$$

$$2CO+4H_2 \rightarrow 2CH_3OH+181.6 \text{ kJ/DME-mol} \quad (3)$$

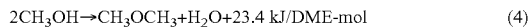
$$2CH_3OH \rightarrow CH_3OCH_3+H_2O+23.4 \text{ kJ/DME-mol} \quad (4)$$

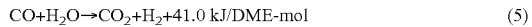
$$CO+H_2O \rightarrow CO_2+H_2+41.0 \text{ kJ/DME-mol} \quad (5)$$

Reaction (1) synthesizes DME from synthesis gas ($H_2$, CO) in three steps: methanol synthesis reaction (3), dehydration reaction (4), and shift reaction (5). When the shift reaction is slow, reactions (3) and (4) are combined into reaction (2). Overall the reaction is exothermic and the reaction heat at methanol synthesis step is dominant.

Another known production method of DME is the catalytic dehydration of methanol according to reaction (4) above. One such process is carried out in an adiabatic reactor with an inlet methanol temperature above 250° C.

It will be appreciated that there is a need in the art for a process for producing DME and more generally a process for producing dialkyl and diaryl ethers which does not require high temperature, pressure, or solid catalysts.

BRIEF SUMMARY OF THE INVENTION

The present invention provides a process for producing a dialkyl or diaryl ether by reacting carbon dioxide with a metal alcoholate. The reaction does not require high temperature, pressure, or solid catalysts. The reaction can be carried out at standard temperature and pressure; however, higher pressures and lower temperatures may facilitate the reaction with carbon dioxide. More specifically, the present invention provides an alternative process for producing DME by reacting carbon dioxide with a sodium methoxide solution in methanol. Sodium alkoxide catalyst present in the glycerol/alcohol phase after transesterfication reaction of oil and alcohol to produce Fatty Acid Methyl Ethyl Esters (FAME) or Fatty Alcohols can also be removed by treatment with carbon dioxide to form dialkylether. Sodium carbonate solid will form that precipitates.

The general method of producing a dialkyl or diaryl ether involves reacting carbon dioxide with a metal alcoholate having the formula, $M(RO)_x$, where "M" is a Group 1, Group 2, or Group 3 metal, "x" is the valence of the metal M, and "R" is a $C_1$ to $C_6$ lower alkyl or aryl. The reaction produces the dialkyl or diaryl ether having a formula, R—O—R, and a metal carbonate having a formula, $M_2CO_3$ (for Group 1 metals), $MCO_3$ (for Group 2 metals), and $M_2(CO_3)_3$ (for Group 3 metals). The metal carbonate is solid and can be removed by filtration, centrifuge, evaporation, or other known industrial techniques. The dialkyl or diaryl ether typically has a lower boiling point than the alcohol solvent and may be recovered as a gas, for lower alkyl ethers, or through conventional distillation or liquid separation techniques for higher alkyl ethers.

When R is an alkyl group it may include, but is not limited to methyl, ethyl, propyl, isopropyl, butyl, t-butyl, pentyl, and hexyl. When R is an aryl group it may include, but is not limited to, phenyl and naphthyl. The alkyl and aryl groups may include other functional groups (e.g. ester-, alcohol-, acid-) within the alkyl or aryl groups.

In some non-limiting embodiments, the dialkyl or diaryl ether reaction may occur at a pressure in the range from 0 to 20 atmospheres, at a pressure in the range from 1 to 6 atmospheres, or at a pressure in the range from 1 to 2 atmospheres. In some non-limiting embodiments, the dialkyl or diaryl ether is produced at a temperature in the range from $-25°$ C. to 70° C. or a temperature in the range from $-25°$ C. to 25° C. $CO_2$ can be added in gaseous form, or liquid $CO_2$ form, or solid dry-ice form or carbonic acid ($H_2O+CO_2$), or (Methanol+$CO_2$), or $CO_2$ dissolved in alcohols, or $CO_2$ dissolved in solvent with high $CO_2$ uptake capacity.

The metal carbonate and alcohol may optionally be recycled to regenerate the metal alcoholate. An electrolytic regeneration process may be used. This may be particularly useful when sodium, lithium, or potassium metals are used and when an electrolytic cell contains an ion conducting membrane selective for such metals.

These features and advantages of the present invention will become more fully apparent from the following description and appended claims, or may be learned by the practice of the invention as set forth hereinafter.

BRIEF DESCRIPTION OF THE SEVERAL DRAWINGS

In order that the manner in which the above-recited and other features and advantages of the invention are obtained and will be readily understood, a more particular description of the invention briefly described above will be rendered by reference to specific embodiments thereof that are illustrated in the appended drawings. Understanding that the drawings depict only typical embodiments of the invention and are not therefore to be considered to be limiting of its scope, the invention will be described and explained with additional specificity and detail through the use of the accompanying drawings in which:

FIG. 1 discloses a process flow diagram for production of dimethyl ether.

DETAILED DESCRIPTION OF THE INVENTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are given, such as examples of reacting carbon dioxide with a metal alcoholate to produce a dialkyl or diaryl ether, to provide a thorough understanding of embodiments of the invention. One having ordinary skill in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The presently preferred embodiments of the present invention will be best understood by reference to the drawing, wherein like parts are designated by like numerals throughout. It will be readily understood that the components of the present invention, as generally described and illustrated in the figure herein, could be arranged and designed in a wide variety of different configurations. Thus, the following more detailed description of the embodiments of the ether production method within the scope of the present invention, as represented in FIG. 1, and is not intended to limit the scope of the invention, as claimed, but is merely representative of presently preferred embodiments of the invention.

The present invention discloses a process for the production of dialkyl and diaryl ethers. The process includes the reaction of carbon dioxide with a metal alcoholate. Virtually any metal alcoholate may be used in the disclosed process. Suitable metal alcoholates may be formed by reaction of an alcohol, in which the proton is acidic, with a sufficiently reactive metal, such as Group 1, Group 2, and certain Group 3 metals.

A general chemical reaction for the production of dialkyl and diaryl ethers according to one embodiment within the scope of the invention is summarized below:

Group 1 Metals—$2MRO + CO_2 \rightarrow M_2CO_3 + R\text{—}O\text{—}R$
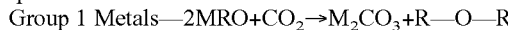
Group 2 Metals—$M(RO)_2 + CO_2 \rightarrow MCO_3 + R\text{—}O\text{—}R$
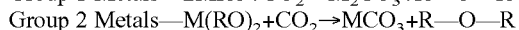
Group 3 Metals—$4M(RO)_3 + 6CO_2 \rightarrow 2M_2(CO_3)_3 + 6R\text{—}O\text{—}R$
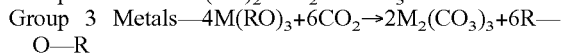

Where "M" is a Group 1, Group 2, or Group 3 metal that forms metal alcoholates; "x" is the valence of the metal M; "R" is selected from $C_1$ to $C_6$ lower alkyl or aryl. Examples of the metal M include, but are not limited to, alkali metals, alkaline earth metals, and aluminum. Examples of alkyl R groups include, but are not limited to, methyl, ethyl, propyl, isopropyl, butyl, t-butyl, pentyl, and hexyl. Examples of aryl R groups include, but are not limited to, phenyl and naphthyl.

While the invention is broadly applicable to the production of dialkyl and diaryl ethers, certain general principles of the invention are disclosed herein in relation to the more specific example of producing dimethyl ether. It being understood that other dialkyl and diaryl ethers may be produced according to the principles disclosed herein.

Referring to FIG. 1, a process flow diagram for reacting sodium methoxide and carbon dioxide to produce DME is disclosed. Electrolytic cell (1) produces sodium methoxide in methanol from sodium carbonate (6), a byproduct from the DME synthesis, and a source of methanol (8). While the following disclosure refers to sodium methoxide, the specified reactions are not limited to sodium methoxide. Other metal alkoxides or metal alcoholates, such as, but not limited to, lithium, potassium, magnesium, and aluminum alkoxide, will also react to from corresponding alkali or aryl carbonates and dialkyl or diaryl ethers.

The electrolytic cell (1) may be a standard cell with a cation conducting membrane that transports sodium ions from the anolyte to the catholyte where the sodium methoxide is generated. One non-limiting example of the cation conducting membrane includes, but is not limited to, metal ion conducting ceramic materials including the type known as MeSICON (Metal Super Ionic CONductor) materials. Where the metal is sodium, NaSICON-type membrane materials may be used. Where the metal is lithium, LiSICON-type membrane materials may be used. Where the metal is potassium, KSICON-type membrane materials may be used.

One non-limiting example of the electrolytic reactions that may occur in electrolytic cell (1) include:

Anode: $Na_2CO_3 \rightarrow 2Na^+ + \frac{1}{2} O_2 + CO_2 + 2e^-$
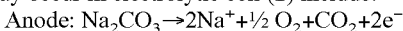
Cathode: $2CH_3OH + 2e^- + 2Na^+ \rightarrow 2NaOCH_3 + H_2$
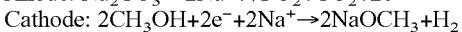
Overall $Na_2CO_3 + 2CH_3OH \rightarrow 2NaOCH_3 + H_2 + \frac{1}{2}O_2 + CO_2$
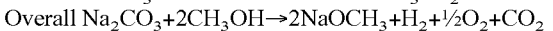

The sodium methoxide (2) produced in electrolytic cell (1) enters a reactor (3). Carbon dioxide from carbon dioxide source (4) also enters reactor (3). In one non-limiting embodiment, carbon dioxide (A) produced in the electrolytic cell (1) may be combined with carbon dioxide from carbon dioxide source (4) and added to the reactor (3). The chemical reaction for the production of DME is summarized below:

$$2NaOCH_3 + CO_2 \rightarrow Na_2CO_3 + CH_3OCH_3$$
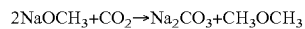

The resulting products are DME and sodium carbonate. In one non-limiting example, the DME formation reaction, and more generally, the dialkyl and diaryl ether formation reaction, may take place at 0 to 20 atmosphere pressures and from $-25°$ C. to $70°$ C. In another non-limiting example, the reaction may occur at a pressure from 1 to 6 atmospheres and a temperature from $-25°$ C. to $25°$ C. In yet another non-limiting example, the reaction may occur at a pressure from 1 to 2 atmospheres.

The specific DME formation reaction, and more generally, the dialkyl and diaryl ether formation reaction may occur in an alcohol solution. The alcohol may or may not be an alkyl or aryl alcohol corresponding to the alkyl or aryl alcoholate. In some cases a different alcohol may be used to aid in carbon dioxide absorption and solubility. A higher concentration of carbon dioxide may facilitate the disclosed reaction. For example, methanol is known to dissolve more carbon dioxide than other alcohols, so methanol may be added to the metal alcoholate solution.

If water is present in sodium methylate/methanol solution as NaOH, the above reaction may be followed by:

$$2NaOH + CO_2 \rightarrow Na_2CO_3 + H_2O$$
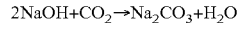

The sodium carbonate is insoluble in methanol and is separated (5) into sodium carbonate (6), methanol, which may be combined with the source of methanol (8), and DME (9). Since DME has a comparatively low boiling point compared to methanol, it is easily separated so that all three phases (gas—DME, liquid—methanol, solid—sodium carbonate) can be collected and purified. The sodium carbonate and methanol may be recycled back to the electrolytic cell (1)

where the sodium methoxide is regenerated, or more broadly, the metal carbonate and alcohol may be recycled back to regenerate the metal alcoholate. The sodium carbonate and methanol are recovered by means of standard industrial separation practices and converted back to the sodium methoxide either by electrolysis or other available methods, one example of which is discussed above.

It is to be understood that the disclosed process does not require the recovery and recycling of metal carbonate or the electrolytic generation of the metal alcoholate. Such process steps may provide certain benefits, but they are optional and may not be practical depending on the choice of alcoholate.

The dimethyl ether produced from the reaction above can be used in any known or novel application, including but not limited to those uses disclosed above. For example, DME may be added to biodiesel or diesel as a fuel additive to improve physical and combustion properties. DME may be a substituted for liquefied petroleum gas (LPG), used as a blended fuel or building block for other fuels or petrochemicals, or reformed into hydrogen for fuel cells. DME may be used as a propellant in aerosol formulations. By analogy, the more general dialkyl and diaryl ethers produced according to the disclosed process may also be used as a fuel, fuel additive, propellant, or building block for other fuels or petrochemicals.

The general reaction disclosed herein between a metal alcoholate and carbon dioxide can be used to sequester carbon dioxide. More specifically, sodium methoxide in methanol and sodium hydroxide in water can also be used to sequester carbon dioxide by the above reactions stated. The carbon dioxide can be sequestered from other processes that produce it or from carbon dioxide already present in the atmosphere.

While specific embodiments and examples of the present invention have been illustrated and described, numerous modifications come to mind without significantly departing from the spirit of the invention, and the scope of protection is only limited by the scope of the accompanying claims.

The invention claimed is:

1. A method of producing a dialkyl or diaryl ether comprising:
    reacting carbon dioxide with a metal alcoholate having the formula, $M(RO)_x$, where "M" is a Group 1, Group 2, or Group 3 metal, "x" is the valence of the metal M, and "R" is an aryl group selected from phenyl and naphthyl, under reaction conditions which produce a dialkyl or diaryl ether having a formula, R—O—R, and a metal carbonate having a formula, $M_2CO_3$ where M is a Group 1 metal, $MCO_3$ where M is a Group 2 metal, and $M_2(CO_3)_3$ where M is a Group 3 metal, wherein the dialkyl or diaryl ether is produced at a temperature in the range from −25° C. to 70° C., and wherein the metal alcoholate is in an alcohol solution;
    removing the metal carbonate; and
    recovering the dialkyl or diaryl ether.

2. The method of claim 1, wherein R is an alkyl group selected from methyl, ethyl, propyl, isopropyl, butyl, t-butyl, pentyl, and hexyl.

3. The method of claim 1, wherein the alcohol has the formula ROH.

4. The method of claim 1, wherein the alcohol is methanol.

5. The method of claim 1, wherein the metal alcoholate is sodium methoxide.

6. The method of claim 1, wherein the dialkyl or diaryl ether is produced at a pressure in the range from 0 to 20 atmospheres.

7. The method of claim 1, wherein the dialkyl or diaryl ether is produced at a pressure in the range from 1 to 6 atmospheres.

8. The method of claim 1, wherein the dialkyl or diaryl ether is produced at a pressure in the range from 1 to 2 atmospheres.

9. The method of claim 1, wherein the dialkyl or diaryl ether is produced at a temperature in the range from −25° C. to 25° C.

10. A method of producing dimethyl ether comprising:
    reacting carbon dioxide with a metal methoxide in methanol, wherein the metal is a Group 1, Group 2, or Group 3 metal, under reaction conditions which produce dimethyl ether and a metal carbonate, wherein the dimethyl ether is produced at a temperature in the range from −25° C. to 70° C.;
    removing the metal carbonate;
    recovering the dimethyl ether; and
    recycling the metal carbonate and methanol to regenerate the metal methoxide.

11. The method of claim 10, wherein the metal methoxide is regenerated electrolytically.

12. The method of claim 10, wherein the metal is selected from sodium, potassium, magnesium, and aluminum.

13. The method of claim 10, wherein the dimethyl ether is produced at a pressure in the range from 0 to 20 atmospheres.

14. The method of claim 10, wherein the dimethyl ether is produced at a pressure in the range from 1 to 6 atmospheres.

15. The method of claim 10, wherein the dimethyl ether is produced at a temperature in the range from −25° C. to 25° C.

16. The method of claim 10, wherein the metal carbonate and methanol are recycled to regenerate the metal methoxide by introducing the metal carbonate and methanol into an electrolytic cell comprising a metal ion conducting ceramic material separating an anode compartment and a cathode compartment, wherein the metal carbonate is introduced into the anode compartment and the methanol is introduced into the cathode compartment.

17. A method of producing a dialkyl or diaryl ether comprising:
    reacting carbon dioxide with a metal alcoholate having the formula, $M(RO)_x$, where "M" is a Group 1, Group 2, or Group 3 metal, "x" is the valence of the metal M, and "R" is a $C_1$ to $C_6$ lower alkyl or aryl, under reaction conditions which produce a dialkyl or diaryl ether having a formula, R—O—R, and a metal carbonate having a formula, $M_2CO_3$ where M is a Group 1 metal, $MCO_3$ where M is a Group 2 metal, and $M_2(CO_3)_3$ where M is a Group 3 metal, wherein the dialkyl or diaryl ether is produced at a temperature in the range from −25° C. to 70° C., wherein the metal alcoholate is in an alcohol solution and the alcohol has the formula ROH;
    recycling the metal carbonate and alcohol to regenerate the metal alcoholate;
    removing the metal carbonate; and
    recovering the dialkyl or diaryl ether.

* * * * *